(12) United States Patent
Zhao et al.

(10) Patent No.: US 12,254,042 B2
(45) Date of Patent: Mar. 18, 2025

(54) INTELLIGENT SURGERY VIDEO MANAGEMENT AND RETRIEVAL SYSTEM

(71) Applicant: Genesis Medtech (USA) Inc., Saint Louis Park, MN (US)

(72) Inventors: Bin Zhao, Ellicott City, MD (US); Ning Li, Pittsburgh, PA (US)

(73) Assignee: GENESIS MEDTECH (USA) INC., Saint Louis Park, MN (US)

( * ) Notice: Subject to any disclaimer, the term of this patent is extended or adjusted under 35 U.S.C. 154(b) by 0 days.

(21) Appl. No.: 18/076,037

(22) Filed: Dec. 6, 2022

(65) Prior Publication Data

US 2023/0177082 A1 Jun. 8, 2023

Related U.S. Application Data

(60) Provisional application No. 63/286,455, filed on Dec. 6, 2021.

(51) Int. Cl.
| | | |
|---|---|---|
| *G06F 16/00* | (2019.01) | |
| *G06F 16/732* | (2019.01) | |
| *G06F 16/78* | (2019.01) | |
| *G06F 16/783* | (2019.01) | |
| *G06T 5/77* | (2024.01) | |
| *G16H 30/40* | (2018.01) | |
| *G16H 70/20* | (2018.01) | |

(52) U.S. Cl.
CPC ...... *G06F 16/7328* (2019.01); *G06F 16/7837* (2019.01); *G06F 16/7867* (2019.01); *G06T 5/77* (2024.01); *G16H 30/40* (2018.01); *G16H 70/20* (2018.01)

(58) Field of Classification Search
CPC ............ G06F 16/7328; G06F 16/7837; G06F 16/7867; G06F 16/783; G06T 5/77; G16H 30/40; G16H 70/20
See application file for complete search history.

(56) References Cited

U.S. PATENT DOCUMENTS

| | | | | |
|---|---|---|---|---|
| 11,080,424 B2* | 8/2021 | Venkataraman | ....... | G16H 10/60 |
| 11,227,686 B2* | 1/2022 | Makrinich | ............. | G06V 20/49 |
| 11,605,161 B2* | 3/2023 | Jin | .......... | G16H 40/20 |
| 11,779,423 B2* | 10/2023 | Roh | ....................... | A61B 34/37 |
| | | | | 606/1 |
| 11,810,356 B2* | 11/2023 | Quist | .................... | G06V 20/46 |

(Continued)

OTHER PUBLICATIONS

International Application No. PCT/US22/51989, International Search Report and Written Opinion mailed May 4, 2023, 14 pages.

*Primary Examiner* — Debbie M Le
(74) *Attorney, Agent, or Firm* — MagStone Law, LLP; Enshan Hong

(57) ABSTRACT

This disclosure describes an intelligent management and retrieval system for surgery videos. The system allows user to upload their surgery videos and provide description of the surgery. A trained machine learning model detects whether there are any privacy leaking segments or frames inside the user uploaded video, and the system removes such privacy information from the video. Medical devices, tissue characteristics and events are detected in the surgery video using trained object recognition, event recognition models. Such detection result, combined with user provided description of the surgery, are utilized to construct rich description of the surgery video.

20 Claims, 5 Drawing Sheets

300

(56) References Cited

U.S. PATENT DOCUMENTS

| | | |
|---|---|---|
| 2015/0082349 A1 | 3/2015 | Ishtiaq et al. |
| 2016/0259888 A1 | 9/2016 | Liu et al. |
| 2020/0372180 A1 | 11/2020 | Venkataraman et al. |
| 2021/0312949 A1* | 10/2021 | Chulev ................. G06T 7/0014 |
| 2022/0328173 A1* | 10/2022 | Mahjouri ............... G16H 30/20 |
| 2023/0245753 A1* | 8/2023 | Kumar .................. G16H 40/67 |
| | | 705/2 |

* cited by examiner

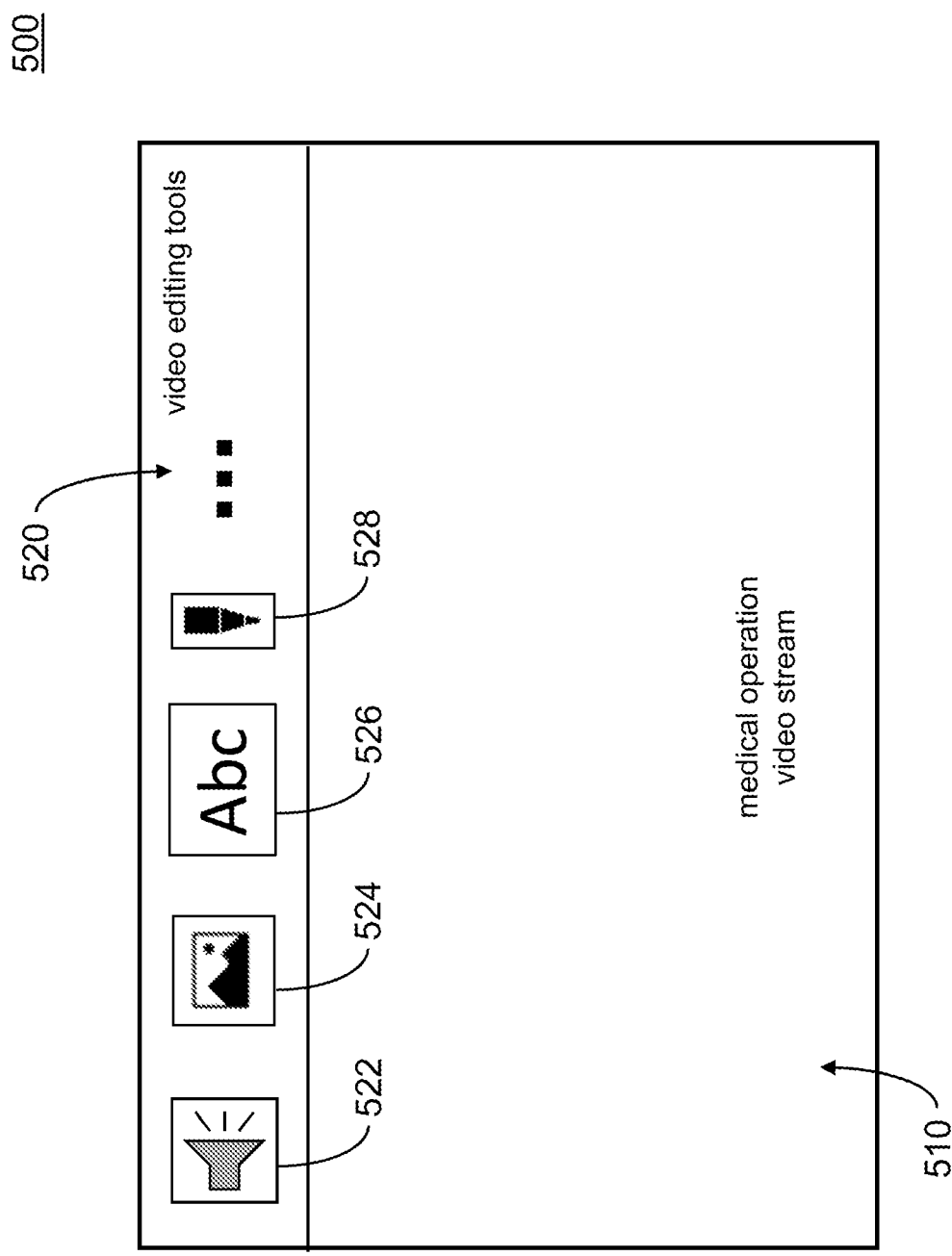

INTELLIGENT SURGERY VIDEO MANAGEMENT AND RETRIEVAL SYSTEM

CROSS-REFERENCE TO RELATED APPLICATIONS

This application claims the benefit of priority to U.S. Provisional Application No. 62/286,455, filed Dec. 6, 2021, the entire disclosure of which is herein incorporated by reference in its entirety for all purposes.

FIELD

This disclosure relates to management and retrieval systems for videos, and more particularly, to intelligent management and retrieval systems for medical operation videos. The medical operations include a wide variety and broad range of operations, and they are not limited to the examples specifically mentioned herein.

BACKGROUND

Surgical videos captured during laparoscopic surgeries contain rich information about the surgery, valuable for surgeon training and surgery preparation. The improvement of scopes and console has resulted in the increasing popularity of laparoscopic surgeries, generating ever growing collection of laparoscopic surgery videos. The high definition and high frame rate of such videos calls for an intelligent management and retrieval system.

SUMMARY

This disclosure is directed to intelligent management and retrieval for videos. The videos may include medical operation videos, such as surgery videos. Some method embodiments may include a method comprising: performing a management process on each medical operation video of a plurality of medical operation videos, the management process comprising: receiving the medical operation video that shows a medical operation performed on a patient in the medical operation video; receiving a description of the medical operation; and detecting a plurality of features from the medical operation video; and performing a retrieval process comprising: receiving a search query for video retrieval; and matching the search query against the plurality of medical operation videos, based on both the descriptions and the detected features of the plurality of medical operation videos.

Some system embodiments may include a system comprising: circuitry configured for: performing a management process on each medical operation video of a plurality of medical operation videos, the management process comprising: receiving the medical operation video that shows a medical operation performed on a patient in the medical operation video; receiving a description of the medical operation; and detecting a plurality of features from the medical operation video; storage for storing the descriptions and the detected features of the plurality of medical operation videos; and said circuitry further configured for: performing a retrieval process comprising: receiving a search query for video retrieval; and matching the search query against the plurality of medical operation videos, based on both the stored descriptions and the stored detected features of the plurality of medical operation videos.

Some non-transitory machine-readable medium embodiments may include a non-transitory machine-readable medium storing instructions, which when executed by one or more processors, cause the one or more processors and/or other processors to perform a method, the method comprising: performing a management process on each medical operation video of a plurality of medical operation videos, the management process comprising: receiving the medical operation video that shows a medical operation performed on a patient in the medical operation video; receiving a description of the medical operation; and detecting a plurality of features from the medical operation video; performing a retrieval process comprising: receiving a search query for video retrieval; matching the search query against the plurality of medical operation videos, based on both the descriptions and the detected features of the plurality of medical operation videos.

In some embodiments, the medical operation comprises a laparoscopic surgery. In some embodiments, the detected plurality of features comprises one or more recognized medical devices appearing in the video, one or more recognized tissue characteristics, movement tracking of objects, or occurrence of one or more certain events during the medical operation. In some embodiments, the management process comprises: detecting portions of the medical operation video having image content of outside the patient's body; and removing or modifying the detected portions having image content of outside the patient's body.

In some embodiments, the search query comprises search text conveying a search need, and said matching the search query retrieves a video or video snippet from among the plurality of medical operation videos, based on the search text conveying the search need. In some embodiments, the search query comprises a search video snippet conveying a search need, and said matching the search query retrieves a return video or return video snippet from among the plurality of medical operation videos, based on the search video snippet conveying the search need. In some embodiments, the retrieval process comprises detecting a plurality of features from the search video snippet, and said matching the search query retrieves the return video or return video snippet from among the plurality of medical operation videos, further based on the detected features from the search video snippet.

BRIEF DESCRIPTION OF THE DRAWINGS

FIG. 5 illustrates a screen layout with video editing tools for medical operation video stream.

DETAILED DESCRIPTION OF PREFERRED EMBODIMENTS

Figure 1:
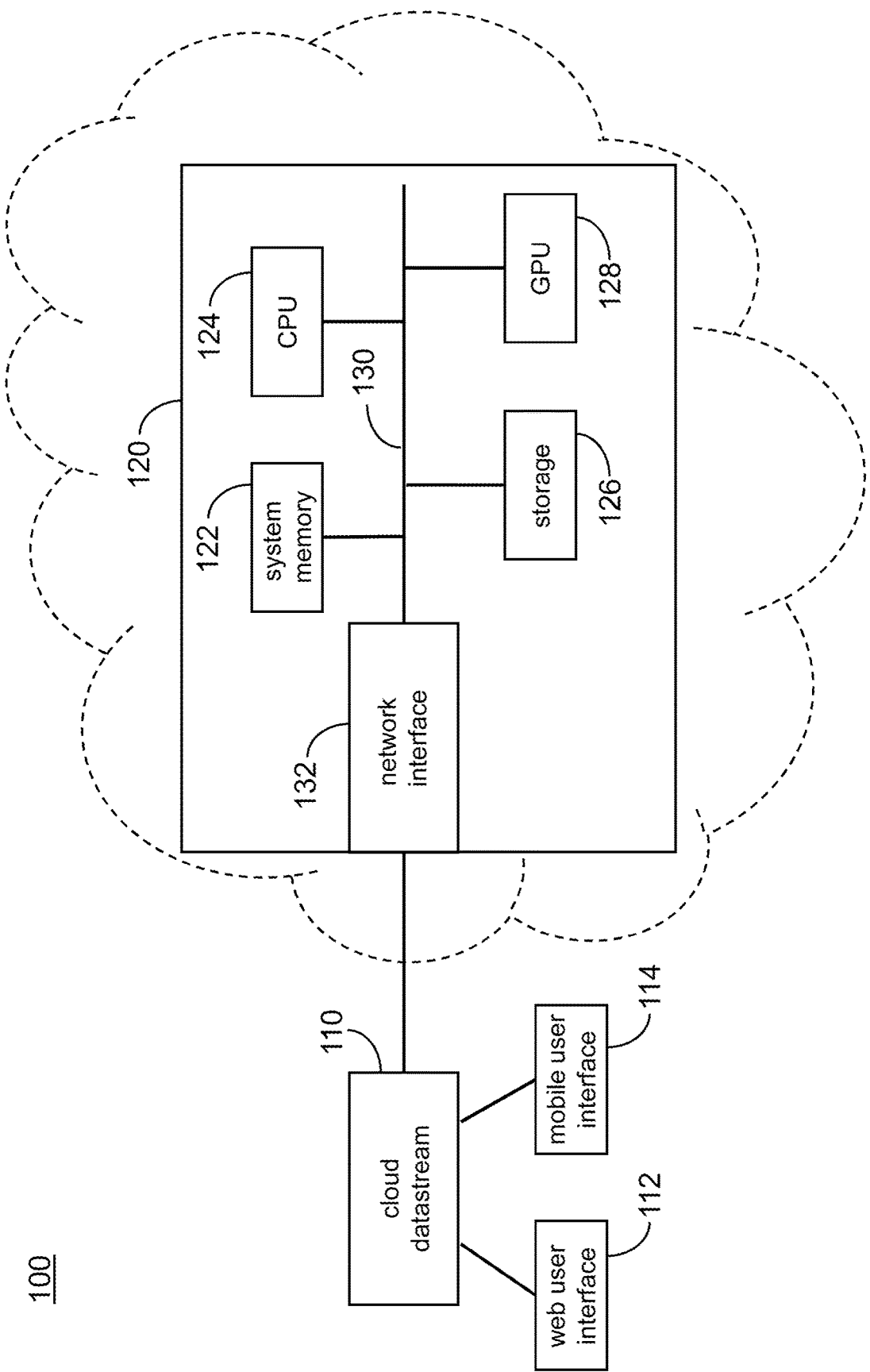
FIG. 1 illustrates an exemplary embodiment of the medical operation video management system 100 with communication network.

This disclosure is not limited to the particular systems, devices and methods described, as these may vary. The terminology used in the description is for the purpose of describing the particular versions or embodiments only, and is not intended to limit the scope. Various examples will now be described. This description provides specific details for a thorough understanding and enabling description of these examples. One skilled in the relevant art will understand, however, various examples may be practiced without many of these details. Likewise, one skilled in the relevant art will also understand that embodiments can include many other obvious features not described in detail herein. Additionally, some well-known structures or functions may not be shown or described in detail herein, so as to avoid unnecessarily obscuring the relevant description.

Laparoscopic surgeries could last for a significant amount of time, generating long surgery videos, causing difficulties for finding relevant information. Some surgery videos could be many hours; it can be routine for surgery videos to be longer than 4 hours. For example, if a surgeon wants to find video segment corresponding to a specific phase of the surgery or when a specific type of medical device is used, the surgeon will need to browse or skim the entire video to locate such segment. The similar visual appearance of the entire surgery video can cause tremendous difficulty in finding such information. Therefore, segmentation, indexing and retrieval functions are needed to enable users to search for desired information within a video or an archive of videos. Users should be able to articulate their query describing the information need, for example, a text query detailing patient description, surgical tools used, surgery phase, or video snippet query seeking similar surgical situations.

This disclosure describes an intelligent management and retrieval system for medical operation videos, such as surgery videos. The system can allow user to upload their medical operation videos (e.g., surgery videos) and provide description of the medical operation (e.g., surgery). A trained machine learning model can detect whether there are any privacy leaking segments or frames inside the user uploaded video, and the system can remove such privacy information from the video. Medical devices, tissue characteristics and events can be detected in the surgery video using trained object recognition, event recognition models. Such detection result, combined with user provided description of the surgery, can be utilized to construct rich description of the surgery video. Videos captured during medical operations (e.g., surgeries) can contain rich information about the operations, valuable for medical training and operation preparation. The rich information here can refer to any knowledge or know-how that can be learned from watching a medical operation video. Examples include how to maneuver surgical instruments or tools (such as a stapler, scalpel, needle driver, etc.) during a specific surgery and how to deal with unexpected events during a surgery, such as unexpected bleeding. The system may construct a rich description of a medical operation video based on rich information from the medical operation video.

To search in the database of surgery videos, user provided query will or may be matched against the rich description of each surgery video in the database, using natural language understanding (NLU) methods, such as sentence embedding model, e.g., USE model, BERT model.

Video management and retrieval system has been well studied: various storage, indexing and fuzzy matching methods have been attempted. The system described in this disclosure may have some or all of the following features:
  1. Detection and removal of privacy revealing segments and frames: Protecting user privacy is paramount in healthcare applications, especially in surgery videos where abundant information is stored. The proposed system may have a module to detect when the scope is outside of patient body. Video segments/frames recorded during such period may be automatically flagged, since patient/surgeon could potentially be identified from those video contents. User can elect to remove those segments or replace them with static (e.g., blue) images.
  2. Automatic analysis on video contents to generate rich description of the surgery video: traditional video retrieval relies on user provided text description to match future query, while treating the video itself as a black box, without understanding the video contents. The proposed system may deploy object recognition and event recognition models to analyze the surgery video, to generate rich detection results, which may then be used to complement user provided description of the surgery. Such detection results will or may then be utilized to match user query in video retrieval function.

FIG. 1 illustrates an exemplary embodiment of the medical operation video management system 100 with communication network. System 100 can provide medical operation videos. System 100 can receive video image frames at a network interface card(s) 130 from a cloud datastream 132 of a cloud network across a network data link, such as Ethernet, etc.

System 100 can perform video management and retrieval at circuitry 120, which may be implemented as a motherboard, a cloud computing network, other computing device, etc. Circuitry 120 may include storage 126 (e.g., hard drive(s), solid-state drive(s), other storage media, database(s), combination of storage devices) to store data, such as the medical operation video(s), data for a machine learning model(s), user-provided data having description of operation, data for a convolutional neural network(s), system software, cloud software, etc. This storage 126 may include one or more storage medium devices that store data involved in the management and retrieval of video contents of the provided medical operation videos. Circuitry 120 may include circuitry 124, e.g., one or more CPUs or other kinds of processors, to execute software or firmware or other kinds of programs that cause circuitry 120 to perform the functions of circuitry 120. Circuitry 120 may include circuity 128, e.g., one or more GPUs, to perform functions for machine learning. The CPU(s) and GPU(s) may perform functions involved in the management and retrieval of video contents of the provided medical operation videos. Throughout this disclosure, functions performed by GPU(s) 128 may also be performed by CPU(s) 124 or by GPU(s) 128 and CPU(s) 124 together. Circuity 124 may include system memory 122 (e.g., RAM, ROM, flash memory, or other memory media) to store data, such as data to operate circuitry 120, data for an operating system, data for system software, data for cloud software, etc. Some or all of the components or elements of circuity 120 may be interconnected via one or more connections 130, like buses, cables, wires, traces, network connections (e.g., wired, wireless), etc.

Users of system 100 can interact with the video management and retrieval functions. Circuitry 120 may connect to web user interface 112 and mobile user interface 114 via communications through network interface 132 and cloud datastream 110. Web user interface 112 and mobile user interface 114 may include user interface(s) and display(s) to receive inputs from and/or provide outputs to the user(s). Such user interface(s) may include, e.g., manual operators like button(s), rotary dial(s), switch(es), touch surface(s), touchscreen(s), stylus, trackpad(s), mouse, scroll wheel(s), keyboard key(s), etc.; audio equipment like microphone(s), speaker(s), etc.; visual equipment like camera(s), light(s), photosensor(s), etc.; any other conventional user interface equipment. Such display(s) can visualize activity related to the video management and retrieval functions. Displays of web user interface 112 and mobile user interface 114 may be housed or integrated with element(s) of external devices, such as in a monitor or a panel display that includes a touchscreen, microphone, speakers, and a camera, to receive user inputs and to provide system outputs to a user.

In some embodiments, circuitry 120 may include programs like an operating system (e.g., Linux) or cloud software to run operations of circuitry 120. In some embodiments, circuitry 120 may include circuitry, e.g., FPGA or ASIC, or some combination of hardware circuitry and software to run operations of circuitry 120. Via some or all of the above components, circuitry 120 can receive medical operation videos and perform video management and retrieval functions of video contents of the medical operation videos.

Figure 2:
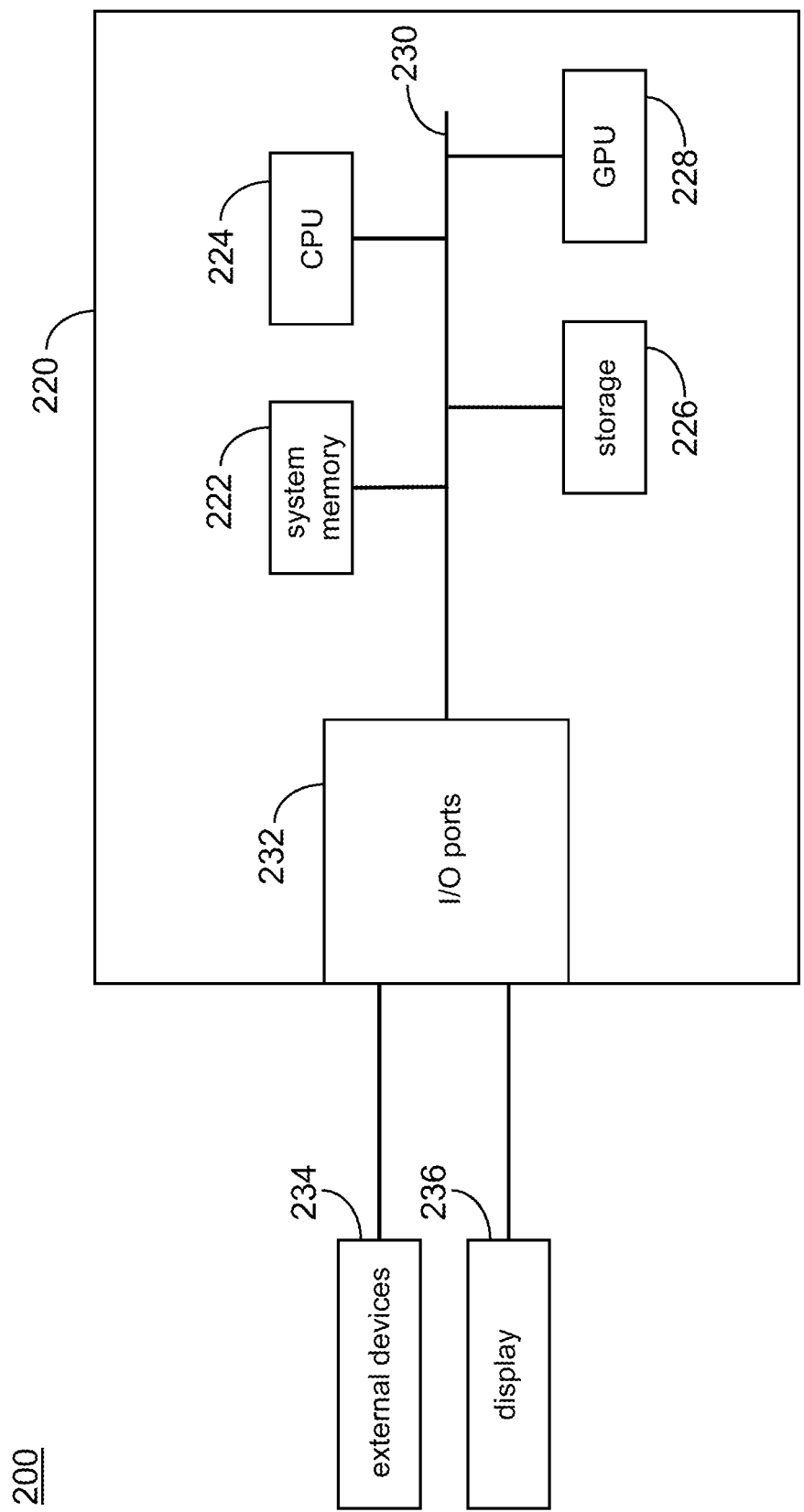
FIG. 2 illustrates an exemplary embodiment of the medical operation video management system 200 with direct connection.

FIG. 2 illustrates an exemplary embodiment of the medical operation video management system 200 with direct connection. System 200 can receive video image frames at I/O ports 232 from external devices 234 (e.g., laptop, desktop computer, smartphone, data storage device, etc.) across a local data link, such as USB, Thunderbolt, etc.

System 200 can perform video management and retrieval at circuitry 220, which may be implemented as a motherboard, other computing device, etc. Circuitry 220 may include storage 226 (e.g., hard drive(s), solid-state drive(s), other storage media, database(s), combination of storage devices) to store data, such as the medical operation video (s), data for a machine learning model(s), user-provided data having description of operation, data for a convolutional neural network(s), system software, etc. This storage 226 may include one or more storage medium devices that store data involved in the management and retrieval of video contents of the provided medical operation videos. Circuitry 220 may include circuitry 224, e.g., one or more CPUs or other kinds of processors, to execute software or firmware or other kinds of programs that cause circuitry 220 to perform the functions of circuitry 220. Circuitry 220 may include circuity 228, e.g., one or more GPUs, to perform functions for machine learning. The CPU(s) and GPU(s) may perform functions involved in the management and retrieval of video contents of the provided medical operation videos. Throughout this disclosure, functions performed by GPU(s) 228 may also be performed by CPU(s) 224 or by GPU(s) 228 and CPU(s) 224 together. Circuity 224 may include system memory 222 (e.g., RAM, ROM, flash memory, or other memory media) to store data, such as data to operate circuitry 120, data for an operating system, data for system software, etc. Some or all of the components or elements of circuity 220 may be interconnected via one or more connections 230, like buses, cables, wires, traces, etc.

Users of system 200 can interact with the video management and retrieval functions. Circuitry 220 may connect to external devices 234 and display 236 via I/O ports 232 to provide the analysis and assessment to the user(s). External devices 122 may include user interface(s) (e.g., manual operators like button(s), rotary dial(s), switch(es), touch surface(s), touchscreen(s), stylus, trackpad(s), mouse, scroll wheel(s), keyboard key(s), etc.; audio equipment like microphone(s), speaker(s), etc.; visual equipment like camera(s), light(s), photosensor(s), etc.; any other conventional user interface equipment) to receive inputs from and/or provide outputs to the user(s). Display 236 can visualize activity related to the video management and retrieval functions. Display 236 may be a basic monitor or display that displays content related to the video management and retrieval functions from circuitry 220 in a visual manner, or a more robust monitor or display system including circuitry that can perform some or all functionalities of circuitry 220 to perform the video management and retrieval functions, in addition to display components that can display content related to the video management and retrieval functions in a visual manner. Display 236 may be a panel display that is housed or integrated with circuitry 220 or a separate display that can communicatively connect with circuitry 220, e.g., via a wired connection or a wireless connection. Display 236 may be housed or integrated with element(s) of external devices 234, such as in a monitor that includes a touchscreen, microphone, speakers, and a camera, to receive user inputs and to provide system outputs to a user.

In some embodiments, circuitry 220 may include programs like an operating system (e.g., Linux) to run operations of circuitry 220. In some embodiments, circuitry 220 may include circuitry, e.g., FPGA or ASIC, or some combination of hardware circuitry and software to run operations of circuitry 220. Via some or all of the above components, circuitry 220 can receive medical operation videos and perform video management and retrieval functions of video contents of the medical operation videos.

The system may be implemented in various form factors and implementations. For example, the system can be deployed on a local machine, e.g., an independent surgery assistant system, or on a PC or workstation. As another example, the system can be deployed in an IT data server with on premise installation. As yet another example, the system will or may be a Software-as-a-Service (SaaS) product, deployed either in a secure public cloud or user's private could. User will or may be provided access to the system through a web user interface or mobile user interface. User can also provision access account to other members in their organization and define what contents are visible to each account.

Figure 3:
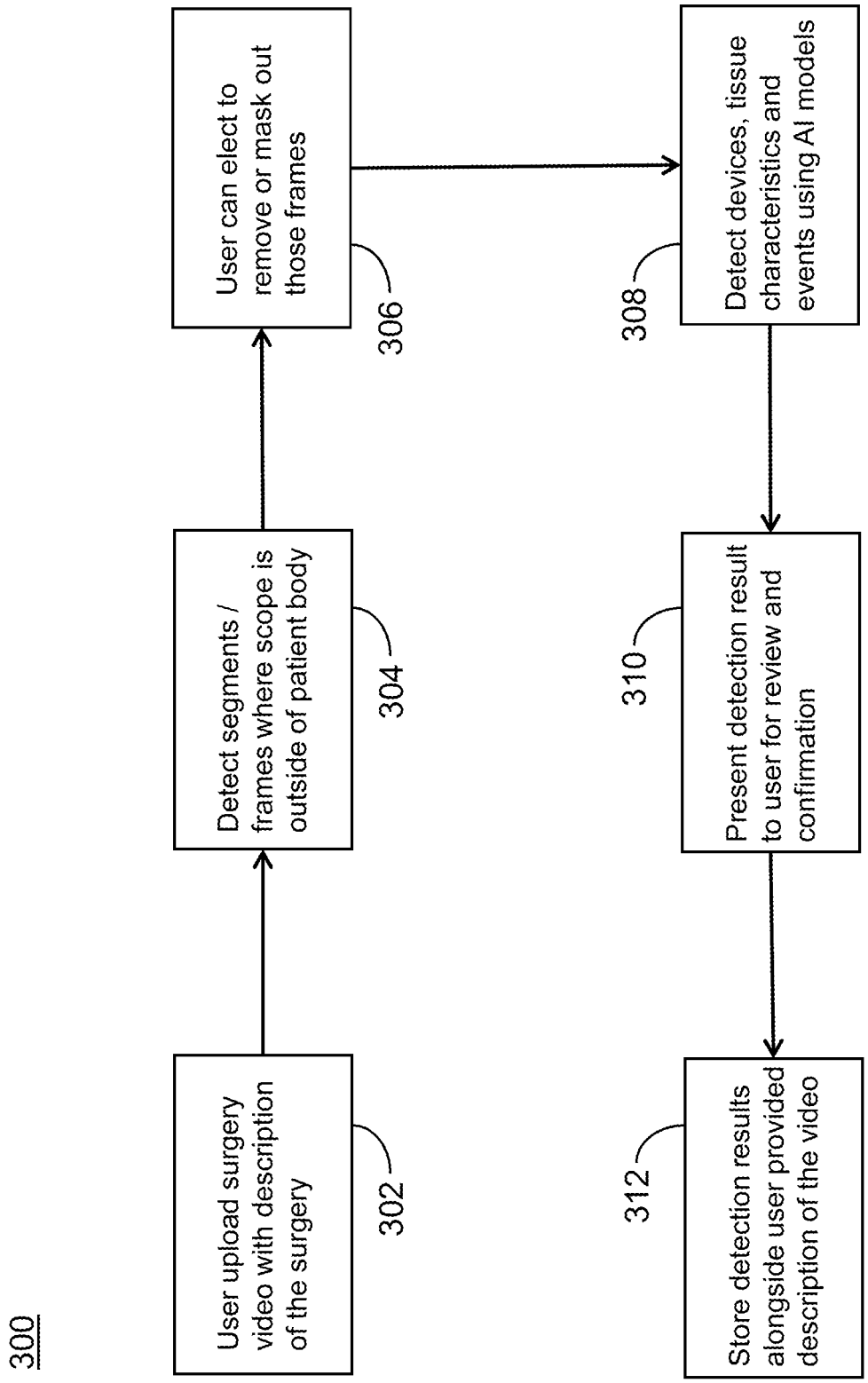
FIG. 3 provides detailed workflow of the surgery video uploading and processing functions.
Figure 4:
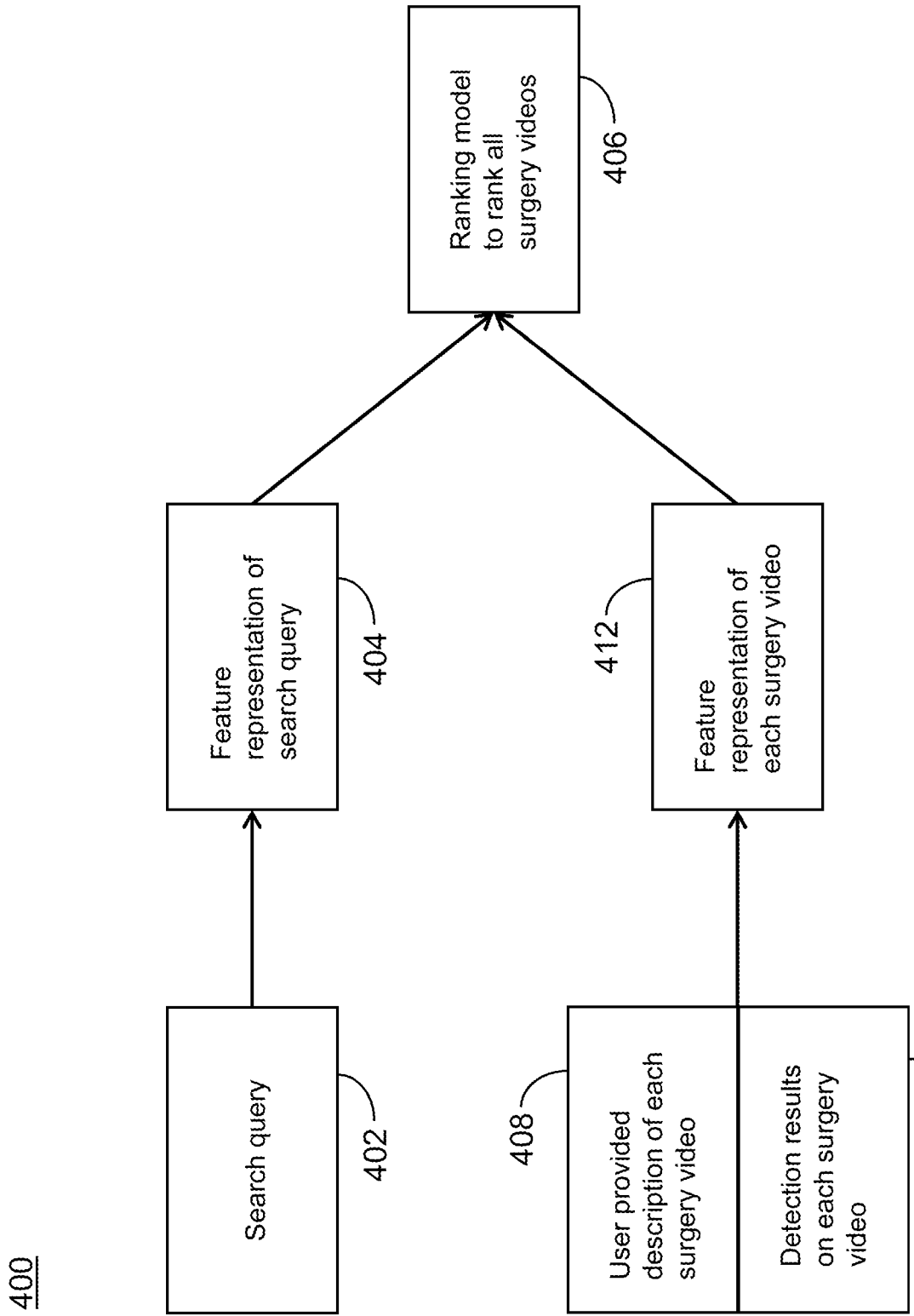
FIG. 4 provides detailed workflow of the video retrieval function.

This disclosure describes a surgical video management system for video management and intelligent retrieval. The system may provide some or all of the following functions, which may be reflected in FIGS. 3-5. FIG. 3 provides detailed workflow 300 of the surgery video uploading and processing functions. FIG. 4 provides detailed workflow 400 of the video retrieval function. FIG. 5 illustrates a screen layout 500 with video editing tools for medical operation video stream.

1. Video storage: The system (e.g., 100, 200) will or may connect to user's archive of surgery videos (e.g., via cloud datastream 110, external devices 234), such as on-premise storage or cloud storage, and the system will or may extract videos from such locations (e.g., step 302). Due to the large size of surgery videos caused by high definition and high frame rate, proper compression scheme could be applied. An exemplary surgery video can be 10 GB or more in data size. Compression can remove repetitive footage or garbage footage from the surgery videos. Example garbage footage may include: video footage when the camera is outside of patient body, video footage when doctor is preparing mesh hence there is no movement in the camera's field of view.
2. Detection and removal of privacy revealing segments and frames: The system will or may detect when video image frames contain privacy-revealing content or not (e.g., when scope is outside of patient body) and flag those segments/frames as potentially leaking privacy information (e.g., step 304). The user can confirm what action to take on those video segments (e.g., step 306), e.g., removal from the video, replacement with static blue images, blurring images (e.g., with a mosaic blur effect). For example, a machine learning model (e.g., a convolutional neural network) can be built and/or trained for or by system 100, 200 to classify a video image frame into 2 image classes: containing potentially privacy-revealing content or not (e.g., inside or outside of patient body). A machine learning model run on GPU(s) 128, 228 may perform the auto-detection and auto-flagging tasks.

3. Intelligent video processing and analysis: The system will or may automatically analyze the video contents using computer vision techniques (e.g., step 308), including recognizing medical devices appearing in each video frame, recognizing tissue characteristics, and tracking its movement. Machine learning model(s) (e.g., convolutional neural network(s)) may be trained for or by system 100, 200 to recognize objects (surgical instruments to tools, anatomical structures) and surgical events. Such model(s) may be applied on the surgery video. The output of the model(s) may be the analysis results. Machine learning model(s) run on GPU(s) 128, 228 may perform the auto-recognition and auto-tracking tasks. Using pre-defined surgery phases/workflow for the specific surgery in the video (see Table 1 for an example surgery phase definition for cholecystectomy), the system will or may automatically divide the surgery video into segments corresponding to such defined phases. A machine learning model can be built and/or trained for or by system 100, 200 to classify a video image frame into one of the pre-defined surgical phases. A machine learning model run on GPU(s) 128, 228 may perform the auto-segmentation task. The system will or may also recognize events such as excessive bleeding in the surgery video. For example, a machine learning model (e.g., convolutional neural network) can be built and/or trained for or by system 100, 200 to detect bleeding imagery in each frame or some frames of the surgery video.

TABLE 1

Workflow of cholecystectomy surgery

| Phase ID | Phase |
|---|---|
| 1 | Preparation |
| 2 | calot triangle dissection |
| 3 | clipping and cutting |
| 4 | gallbladder dissection |
| 5 | gallbladder packaging |
| 6 | cleaning and coagulation |
| 7 | gallbladder retraction |

Systems 100, 200 can present the results of various detection tasks above to a user (e.g., steps 306, 310). The results may be presented to user(s) via a display and/or outputs of web user interface 112, or via a display and/or outputs of mobile user interface 114, or via display 236 and/or outputs of user interface(s) among external devices 234. A user can interact with systems 100, 200 (e.g., via web user interface 112, mobile user interface 114, or external devices 234 such as user interface(s) that can receive inputs from the user). For example, in response to reviewing detected and flagged video segments as potentially leaking privacy information (e.g., from step 304), a user can confirm what action to take on those video segments (e.g., step 306). As another example, in response to reviewing detected aspects from video analysis (e.g., from step 308), a user can confirm some of all of those detected aspects (e.g., step 310).

Systems 100, 200 can store the results of various detection tasks on a medical operation video, alongside user-provided description(s) of the medical operation video (e.g., step 312). The results may be stored in storage 126, 226, such as in a database(s). Such detection results (e.g., for step 410) may be used to complement the user-provided description(s) of the medical operation video (e.g., for step 408), e.g., description of a surgery in the video. Such detection results may be utilized to match user query in video retrieval function(s). Such detection results, combined with user-provided descriptions of the medical operation, can be utilized to construct rich description (e.g., for step 412) of the medical operation video.

4. Video retrieval: The system will or may support retrieval of surgery video or video segments using 2 types of queries:
 a. Text query: User can provide description of search need (e.g., step 402) including surgery type, surgery phase, medical device usage, patient information, and the system will or may provide video segments matching such query (e.g., step 406). Each text query would or could be embedded to semantic space using sentence embedding techniques such as USE or BERT (e.g., step 404). Feature representation of the search query may be a vector, matrix, and/or tensor representation of the text content of the text search query.

USE model stands for "universal sentence encoder model," which is a neural network model that embeds natural language sentences into a mathematical high dimensional space. The system can provide a mechanism to compare the semantic meaning of 2 or more sentences, e.g., by computing the distance between their representations (represented as vector in high dimensional space). If the distance between 2 sentences is large, it may mean they are more dissimilar in meaning; otherwise if the distance is small, they may have more similar meanings. BERT stands for "bidirectional encoder representations from transformers," and is another model for sentence embedding.

A user can provide text queries to system 100, 200, e.g., via web user interface 112, mobile user interface 114, or external devices 234, such as user interface(s) that can receive inputs from the user to convey text (e.g., keyboard input, touchscreen input, speech-to-text input, etc.). Such text information may be stored (e.g., via storage 126, 226) by the system and transformed into numerical features through natural language understanding models such as sentence embedding (USE or BERT, etc.). An NLU model run on GPU(s) 128, 228 may perform the text-into-numerals transformation task. Those numerical features can be used as a search index, and can be used in intelligent search function(s).

To search in the database of medical operation videos, a user-provided text query may be matched against the rich description for each medical operation video in the database (e.g., step 412), using natural language understanding (NLU) methods, such as sentence embedding model, e.g., USE model, BERT model. A machine learning model can be built and/or trained for or by system 100, 200 to rank all the surgery videos (e.g., step 406), based on an input feature representation of the text search query and on input feature representations of each surgery video, into search results for the user to review. The feature representations of the surgery videos (e.g., for step 412) may be based on the results of the various detection tasks performed on the medical operation videos of the user's archive (e.g., from step 410) and based on the user-provided descriptions of the medical operation videos (e.g., from step 408). A machine learning model run on GPU(s) 128, 228 may perform the ranking task. The search results may be presented to user(s) via a display and/or outputs of web user interface 112, or via a display and/or outputs of mobile user interface 114, or via display 236 and/or outputs of user interface(s) among external devices 234.

b. Video snippet query: User can upload (e.g., via cloud datastream 110, external devices 234) a short video snippet as query (e.g., step 402) to find situations (e.g., step 406) similar to the one in the query video. Such function could support decision making and surgery preparation by showing how other surgeons handled a similar exceptional situation. Each video snippet query would or could first be processed using the same object detection, event detection models used on surgery videos, to extract textual description of the video snippet. Then the detection results would or could be embedded to semantic space using sentence embedding techniques such as USE or BERT (e.g., step 404). Feature representation of the search query may be a vector, matrix, and/or tensor representation of the image content of the video snippet search query.

To search in the database of medical operation videos, a user-provided video snippet query may be matched against the rich description for each medical operation video in the database (e.g., step 412), using natural language understanding (NLU) methods, such as sentence embedding model, e.g., USE model, BERT model. A machine learning model can be built and/or trained for or by system 100, 200 to rank all the surgery videos (e.g., step 406), based on an input feature representation of the video snippet search query and on input feature representations of each surgery video, into search results for the user to review. The feature representations of the surgery videos (e.g., for step 412) may be based on the results of the various detection tasks performed on the medical operation videos of the user's archive (e.g., from step 410) and based on the user-provided descriptions of the medical operation videos (e.g., from step 408). A machine learning model run on GPU(s) 128, 228 may perform the ranking task. The search results may be presented to user(s) via a display and/or outputs of web user interface 112, or via a display and/or outputs of mobile user interface 114, or via display 236 and/or outputs of user interface(s) among external devices 234.

5. User feedback: The system will or may record/log (e.g., via storage 126, 226, such as a database(s)) user click through on returned search results, and may use such user feedback information to retrain the retrieval model for further improvement. The system could also ask user to identify whether the returned video is relevant to the search query and use such label for model fine tuning. A machine learning model can be built and/or trained for or by system 100, 200 to perform the video retrieval. A machine learning model run on GPU(s) 128, 228 may perform the video retrieval task.

6. Video editing: After a medical operation video is uploaded (e.g., via cloud datastream 110 to storage 126, via external devices 234 to storage 226), the system may provide video editing tools or functionalities to the user. A user can provide editing inputs to system 100, 200, e.g., via web user interface 112, mobile user interface 114, or external devices 234, such as user interface(s) that can receive inputs from the user to convey editing actions (e.g., keyboard input, mouse input, trackpad input, touchscreen input, stylus input, camera input, microphone input, etc.). The inputted editing can be performed by processing elements (e.g., circuitry 124, CPU(s)) of system 100, 200. The system can provide the following video editing examples, as shown in FIG. 5 that shows an example screen layout 500 with video editing tools in top panel/toolbar 520 for the medical operation video stream in main panel 510.

a. Insert/add audio overlay into the video 522: for example, user can insert or add audio content to explain what the user is doing or what is occurring in the surgery video.

b. Insert/add image into the video 524: for example, user can insert image content (e.g., presentation slides, photos, drawings, diagrams, etc.) into the surgery video to explain the reasoning for the user's actions or to explain what is occurring in the surgery video.

c. Insert/add text box into video 526: for example, user can insert or add text onto video image frames to explain the user's actions or tools used, or to name an anatomical structure in the surgery video.

d. Drawing on the video 528: for example, user can use a pen stylus tool to freely draw on a video image frame to add visual elements to explain the user's actions or what is occurring in the surgery video, such as highlighting important anatomical regions.

Exemplary embodiments are shown and described in the present disclosure. It is to be understood that the embodiments are capable of use in various other combinations and environments and are capable of changes or modifications within the scope of the concepts as expressed herein. Some such variations may include using programs stored on non-transitory computer-readable media to enable computers and/or computer systems to carry our part or all of the method variations discussed above. Such variations are not to be regarded as departure from the spirit and scope of the invention, and all such modifications as would be obvious to one skilled in the art are intended to be included within the scope of the following claims.

What is claimed is:

1. A method comprising:
performing a management process on each medical operation video of a plurality of medical operation videos, the management process comprising:
receiving the medical operation video that shows a medical operation performed on a patient in the medical operation video;
receiving, after the medical operation video had been created, a user-provided text description of the medical operation performed in the medical operation video;
detecting a plurality of features from the medical operation video;
generating a rich description of the medical operation video based on the after-video-creation text description of the medical operation and detected features from the medical operation video, wherein the rich description provides content information about what is in video contents of the medical operation video, wherein the content information is distinct from and complements the user-provided text description; and
performing a retrieval process comprising:
receiving a search query for video retrieval; and
matching the search query against the rich descriptions of the plurality of medical operation videos, based on both the descriptions and the detected features of the plurality of medical operation videos.

2. The method of claim 1, wherein the detected plurality of features comprises one or more recognized medical devices appearing in the video, one or more recognized tissue characteristics, movement tracking of objects, or occurrence of one or more certain events during the medical operation.

3. The method of claim 1, the management process comprising:
 detecting portions of the medical operation video having image content of outside the patient's body; and
 removing or modifying the detected portions having image content of outside the patient's body.

4. The method of claim 1, wherein:
 the search query comprises a search video snippet conveying a search need, and
 said matching the search query retrieves a return video or return video snippet from among the plurality of medical operation videos, based on the search video snippet conveying the search need.

5. The method of claim 4, wherein:
 the retrieval process comprises detecting a plurality of features from the search video snippet, and
 said matching the search query retrieves the return video or return video snippet from among the plurality of medical operation videos, further based on the detected features from the search video snippet.

6. The method of claim 5, wherein:
 the retrieval process comprises determining a textual description of the search video snippet, based on the detected plurality of features from the search video snippet, and
 said matching the search query retrieves the return video or return video snippet from among the plurality of medical operation videos, further based on the extracted textual description, which is based on the detected features from the search video snippet.

7. The method of claim 6, wherein:
 determining the textual description of the search video snippet comprises embedding the detected plurality of features from the search video snippet to semantic space using one or more sentence embedding techniques.

8. A system comprising:
 circuitry configured for:
  performing a management process on each medical operation video of a plurality of medical operation videos, the management process comprising:
   receiving the medical operation video that shows a medical operation performed on a patient in the medical operation video;
   receiving, after the medical operation video had been created, a user-provided text description of the medical operation performed in the medical operation video;
   detecting a plurality of features from the medical operation video;
   generating a rich description of the medical operation video based on the after-video-creation text description of the medical operation and detected features from the medical operation video, wherein the rich description provides content information about what is in video contents of the medical operation video, wherein the content information is distinct from and complements the user-provided text description;
   storage for storing the descriptions and the detected features of the plurality of medical operation videos; and
 said circuitry further configured for:
  performing a retrieval process comprising:
   receiving a search query for video retrieval; and
   matching the search query against the rich descriptions of the plurality of medical operation videos, based on both the stored descriptions and the stored detected features of the plurality of medical operation videos.

9. The system of claim 8, wherein the detected plurality of features comprises one or more recognized medical devices appearing in the video, one or more recognized tissue characteristics, movement tracking of objects, or occurrence of one or more certain events during the medical operation.

10. The system of claim 8, the management process comprising:
 detecting portions of the medical operation video having image content of outside the patient's body; and
 removing or modifying the detected portions having image content of outside the patient's body.

11. The system of claim 8, wherein:
 the search query comprises a search video snippet conveying a search need, and
 said matching the search query retrieves a return video or return video snippet from among the plurality of medical operation videos, based on the search video snippet conveying the search need.

12. The system of claim 11, wherein:
 the retrieval process comprises detecting a plurality of features from the search video snippet, and
 said matching the search query retrieves the return video or return video snippet from among the plurality of medical operation videos, further based on the detected features from the search video snippet.

13. The system of claim 12, wherein:
 the retrieval process comprises determining a textual description of the search video snippet, based on the detected plurality of features from the search video snippet, and
 said matching the search query retrieves the return video or return video snippet from among the plurality of medical operation videos, further based on the extracted textual description, which is based on the detected features from the search video snippet.

14. The method of claim 13, wherein:
 determining the textual description of the search video snippet comprises embedding the detected plurality of features from the search video snippet to semantic space using one or more sentence embedding techniques.

15. A non-transitory machine-readable medium storing instructions, which when executed by one or more processors, cause the one or more processors and/or other processors to perform a method, the method comprising:
 performing a management process on each medical operation video of a plurality of medical operation videos, the management process comprising:
  receiving the medical operation video that shows a medical operation performed on a patient in the medical operation video;
  receiving, after the medical operation video had been created, a description of the medical operation;
  detecting a plurality of features from the medical operation video;

generating a rich description of the medical operation video based on the after-video-creation text description of the medical operation and detected features from the medical operation video, wherein the rich description provides content information about what is in video contents of the medical operation video, wherein the content information is distinct from and complements the user-provided text description; and performing a retrieval process comprising:
receiving a search query for video retrieval;
matching the search query against the rich descriptions of the plurality of medical operation videos, based on both the descriptions and the detected features of the plurality of medical operation videos.

16. The non-transitory machine-readable medium of claim 15, wherein the detected plurality of features comprises one or more recognized medical devices appearing in the video, one or more recognized tissue characteristics, movement tracking of objects, or occurrence of one or more certain events during the medical operation.

17. The non-transitory machine-readable medium of claim 15, the management process comprising:
detecting portions of the medical operation video having image content of outside the patient's body; and
removing or modifying the detected portions having image content of outside the patient's body.

18. The non-transitory machine-readable medium of claim 15, wherein:
the search query comprises a search video snippet conveying a search need, and
said matching the search query retrieves a return video or return video snippet from among the plurality of medical operation videos, based on the search video snippet conveying the search need.

19. The non-transitory machine-readable medium of claim 18, wherein:
the retrieval process comprises detecting a plurality of features from the search video snippet, and
said matching the search query retrieves the return video or return video snippet from among the plurality of medical operation videos, further based on the detected features from the search video snippet.

20. The non-transitory machine-readable medium of claim 19, wherein:
the retrieval process comprises determining a textual description of the search video snippet, based on the detected plurality of features from the search video snippet, and
said matching the search query retrieves the return video or return video snippet from among the plurality of medical operation videos, further based on the extracted textual description, which is based on the detected features from the search video snippet.

* * * * *